US00RE41946E

(19) United States
(12) Reissued Patent
Anderson et al.

(10) Patent Number: US RE41,946 E
(45) Date of Reissued Patent: Nov. 23, 2010

(54) PORTABLE IMMEDIATE RESPONSE MEDICAL ANALYZER HAVING MULTIPLE TESTING MODULES

(75) Inventors: Carter R. Anderson, Inver Grove Heights, MN (US); David T. Giddings, Carmel, IN (US); James D. Kurkowski, Roseville, MN (US); Robbi T. Thompson, Lake Elmo, MN (US); Kee Van Sin, Lino Lakes, MN (US)

(73) Assignee: International Technidyne Corporation, Piscataway, NH (US)

(21) Appl. No.: 10/153,081

(22) Filed: May 22, 2002

Related U.S. Patent Documents

Reissue of:
(64) Patent No.: 6,066,243
Issued: May 23, 2000
Appl. No.: 09/119,983
Filed: Jul. 21, 1998

U.S. Applications:
(60) Provisional application No. 60/053,406, filed on Jul. 22, 1997.

(51) Int. Cl.
*G01N 27/327* (2006.01)

(52) U.S. Cl. ..... 205/792; 204/403.01; 204/412; 422/82.01

(58) Field of Classification Search ..... 204/403.01, 204/403.04, 412; 422/82.01, 82.03, 82.05, 422/58, 50; 205/777.5
See application file for complete search history.

(56) References Cited

U.S. PATENT DOCUMENTS

| | | | | |
|---|---|---|---|---|
| 4,225,410 | A | 9/1980 | Pace | 204/412 |
| 4,762,594 | A | 8/1988 | Guruswamy | 205/792 |
| 4,935,106 | A | 6/1990 | Liston et al. | 205/778 |

(Continued)

FOREIGN PATENT DOCUMENTS

| | | | |
|---|---|---|---|
| DE | 693 23 094 | | 6/1999 |
| EP | 0 157 597 | | 5/1990 |
| EP | 0 601 589 | A2 | 6/1994 |
| EP | 1 099 114 | | 11/2004 |
| WO | WO 89/00024 | | 1/1989 |
| WO | 94/19683 | | 1/1994 |
| WO | WO 94/19683 | | 9/1994 |
| WO | WO 94/19684 | | 9/1994 |
| WO | 94/19684 | | 9/1994 |
| WO | WO 95/02189 | | 1/1995 |
| WO | WO 97/44672 | | 11/1997 |
| WO | 97/44672 | | 11/1997 |
| WO | WO 98/47423 | | 10/1998 |
| WO | WO 00/05581 | | 2/2000 |

OTHER PUBLICATIONS

User's Reference Manual, Agilent Component Monitoring System, "Chapter 1: The Agilent CMS, V24 and V26 Monitors," pp. 1–38; "Chapter 27: Blood Analysis," pp. 1–22; published before Jul. 21, 1998.

(Continued)

*Primary Examiner*—Alex Noguerola
(74) *Attorney, Agent, or Firm*—Fish & Richardson P.C.

(57) ABSTRACT

A portable device that includes a plurality of test modules for analyzing preselected concentrations of various body fluids of a patient. The portable diagnostic device interfaces and utilizes disposable cartridges and reagent diagnostic test strips and other fluid sample diagnostic devices to determine the amounts of preselected parameters in a patient's blood through either electrochemical, electrical, optical, or mechanical analysis. The disposable fluid sample diagnostic devices may include sample chambers with inlet ports, electrical, physical, or chemical sensors, in situ calibration media, a plurality of electrical interface terminals, and temperature control elements. An electrical interface interconnects the various test modules with one or more corresponding integrated circuits which in turn are electrically coupled to a common interactive display, printer, power supply, and communication ports.

67 Claims, 14 Drawing Sheets

U.S. PATENT DOCUMENTS

| | | | | |
|---|---|---|---|---|
| 5,017,339 | A | 5/1991 | Marsoner et al. | 204/403.02 |
| 5,074,977 | A | 12/1991 | Cheung et al. | 205/775 |
| 5,377,128 | A | 12/1994 | McBean | 702/91 |
| 5,563,042 | A | 10/1996 | Phillips et al. | 435/14 |
| 5,591,403 | A | 1/1997 | Gavin et al. | 422/73 |
| 5,781,024 | A | 7/1998 | Blomberg et al. | 324/763 |
| 6,066,243 | A | 5/2000 | Anderson et al. | 422/82.01 |

OTHER PUBLICATIONS

Benutzerhandbuch [User Handbook] AVL OMNI™ 1–9 Modular System, Revision 7.0 dated Apr. 1998, first edition May 1995, 179 pages.

Serviceanleitung [Service Instructions] AVL OMNI™ 1–9 Modular System, Revision 7.0 dated May 1998, first edition Jun. 1995, 249 pages.

Shepherd and Steinke, "CO–Oximetry interference by perflubron emulsion: comparison of hemolyzing and nonhemolyzing instruments," *Clin. Chem.,* 1998, 44(10):2183–2190.

Kurzbeschreibung (Brief description) IL GEM Premier 3000 and GEM Premier 3100 Workstation and GEM PCL (from Instrumentation Laboratory), date unknown, 35 pages.

Coagulation Analyzers (Survey of Instruments), *CAP Today,* Feb. 1999, 13(2):65–70.

Coagulation Analyzers (Survey of Instruments), *CAP Today,* Aug. 2002, 16(8):52–58.

McConnell, "Getting up to speed with point–of–care blood testing," *Nursing,* Sep. 1998, 3 pages.

IL GEM Premier 3000 Blood Gas Analyzer (product description on homepage http://www.gmi–inc.com/CliniLab/IL%20GEM%20Premier%203000%20Blood%20Gas.html), printed from the internet on Aug. 22, 2005, 3 pages.

Radiometer ABL500 & KNA2 Analyzer (product description on http://www.surrey.ac.uk/GMEC/Pages/GuildfordEvaluations/PreviousReports/Reports/RadiometerABL500.html), printed from the internet on Aug. 22, 2005, 2 pages.

Bizouarn et al., "Comparison between oxygen consumption calculated by Fick's principle using a continuous thermodilution technique and measured by indirect calorimetry," *Br. J. Anaesth.,* 1995, 75(6):719–723.

Bundgaard et al., "$K^+$ supplementation increases muscle [$Na^+$–$K^+$–ATPase] and improves extrarenal $K^+$ homeostasis in rats," *J. Appl. Physiol.,* 1997, 82(4):1136–1144.

AVL 995 Blood Gas Analyzer (product description on homepage http://www.gmi–inc.com/Products/AVLbloodgasmod995.htm), printed from internet on Aug. 22, 2005, 2 pages.

PORTABLE IMMEDIATE RESPONSE MEDICAL ANALYZER HAVING MULTIPLE TESTING MODULES

Matter enclosed in heavy brackets [ ] appears in the original patent but forms no part of this reissue specification; matter printed in italics indicates the additions made by reissue.

The present application is a complete application claiming priority based on co-pending Provisional Application Ser. No. 60/053,406, filed Jul. 22, 1997 and entitled "IMMEDIATE RESPONSE MEDICAL ANALYZER HAVING MULTIPLE TEST MODULES".

BACKGROUND OF THE INVENTION

1. Field of the Invention

The present invention is directed generally to a stationary or portable diagnostic system or electroanalytical systems for analyzing preselected characteristics of a patient's blood and other fluids. More particularly the present invention is concerned with a portable diagnostic device or analytic instrument that includes a plurality of test modules for analyzing various body fluids of a patient, wherein the modules are coupled to a common display, printer, power supply, and communication ports. The portable diagnostic device interfaces and utilizes disposable cartridges, reagent diagnostic test strips, or other means to determine, for example, a patient's blood pH, $pO_2$, $pCO_2$, $Na^+$, $Ca^{++}$, $K^+$, hematocrit, glucose and/or other parameters including oxygen saturation, coagulation or hemoglobin fractions. The modules may determine the parameters through a variety of methods such as electrochemical, electrical, optical, or mechanical analysis of a fluid biological sample extracted from the patient. The disposable cartridge may utilize a bank of sensors for the pertinent electroactive species to provide input in the form of analog electrical signals for the relevant determinations.

II. Related Art

During clinical, surgical, diagnostic and other medical procedures the measurement of certain physical/chemical characteristics or conditions of the blood and other fluids of a patient are useful in order to evaluate the condition of a patient. For example, a patient's blood pH, $pO_2$, $pCO_2$, $Na^+$, $Ca^{++}$, $K^+$, hematocrit, glucose and other parameters including oxygen saturation coagulation or hemoglobin fractions may be measured. These conditions may provide important indications of the patient's stability including, for example, the efficiency of the blood/gas exchange occurring in the lungs of the patient, the relative acid/base balance, or the concentration of certain indicative ion species in the blood. Such determinations are particularly useful in emergency circumstances.

In the past, the equipment provided to make such determinations has typically been complex and permanently installed in a hospital laboratory. Also, the user operating the equipment has been oftentimes required to be a highly-trained and skilled technician, which thereby increases the cost of operating the equipment and limits the number of potential users. With such equipment, in order to analyze a sample of fluid from the patient, a sample must be drawn from the patient and delivered to the laboratory, avoiding all external contacts.

During the transfer and delivery, the drawn fluids may be kept in close proximity to ice packs in order to maintain sample integrity. The sample is then injected into a designated receptacle of the diagnostic equipment and the equipment operated to perform the diagnostics on the sample.

This procedure is time consuming, labor intensive, and usually disadvantageous in the operating room, emergency room or other area of the hospital, or outside the hospital where time is of the essence. Hence, portable devices that reduce the time required to make accurate blood-gas and related determinations, in order that proper and more timely corrective steps may be taken, are highly sought.

Many situations arise where it is impractical to deliver a patient's fluid sample to a hospital laboratory in order to analyze the patient's blood analytes. It would be desirable for paramedics and in-home health care providers, for example, to analyze a sample at the point of collection without having to first deliver a sample to a hospital laboratory. To this end, it would also be desirable to provide a single portable diagnostic device capable of analyzing simultaneously several samples and/or conducting several electrochemical, electrical, optical, or mechanical analysis simultaneously or in rapid succession to determine, a patient's blood pH, $pO_2$, $pCO_2$, $Na^+$, $Ca^{++}$, $K^+$, hematocrit, glucose and other parameters including oxygen saturation, coagulation or hemoglobin fractions.

There have been attempts at point-of-care blood-gas analysis. One on-site analytic device, described by Enzer et al in U.S. Pat. No. 4,786,394, is designed for direct connection to a heart/lung machine to monitor critical blood gases during open-heart surgery. It employs a discardable sensor cartridge which contains a bank of sensors for making the electrochemical determinations. A further patent to Enzer et al (U.S. Pat. No. 4,397,725) also discloses a clinical blood chemistry analyzer in which a discardable cartridge interfaces with an analytical machine. Although the analyzer may be utilized on-site during surgery, the device disclosed by Enzer remains relatively stationary and immobile. Morris et al in U.S. Pat. No. 5,325,853 (of common assignment with the present invention) disclose a self-calibrating disposable sensor system.

Carter et al in U.S. Pat. No. 5,628,890 describe an electrochemical sensor for measuring the glucose concentration in a patient's blood. Such a sensor is limited to the particular analyte being measured and requires an interface with an electrochemical sensor. Stark in U.S. Pat. No. 5,433,197 describes a non-invasive glucose measurement device that requires illumination of the patient's eye with near infrared radiation. The capability of the Stark device is limited to determining blood glucose. Phillips et al in U.S. Pat. No. 5,563,042 describe a device that measures glucose concentration in whole blood optically using a reflective reading apparatus and a whole blood glucose test strip.

A further reference is contained in U.S. Pat. No. 4,849,340 to Oberhardt discloses a device that measures coagulation in whole blood using a liquid assay device and method.

Although somewhat useful, such devices are limited in application and address only part of the drawbacks of prior systems. There remains a need for a rapidly responding, portable blood chemistry analytical device. A need also exists for a single, portable, self-calibrating, instant activation, rapid response diagnostic device capable of simultaneous analysis of several samples and/or conducting several electrochemical, electrical, optical, or mechanical analysis simultaneously or in rapid succession to determine, blood pH, $pO_2$, $pCO_2$, $Na^+$, $Ca^{++}$, $K^+$, hematocrit, glucose and other parameters including oxygen saturation, coagulation or hemoglobin fractions. The present invention meets these needs and overcomes the disadvantages of prior devices.

SUMMARY OF THE INVENTION

The present invention provides a point-of-care medical analyzer that enables an operator without special training or skills to obtain rapid, accurate blood-gas, glucose, and other analyte determinations at the time and location the sample is drawn. The device is compact, light-weight, easily transported and ready for immediate use. The analyzer is designed for rapid processing of electrical signals generated by electrochemical, electrical, optical, or mechanical sensors of an associated module having both calibration and sample determination modes and utilizing one-time use or disposable cartridges. The modules may be removed from the analytic device and interchanged.

The plug-in disposable electrochemical sensor cartridge which may be similar to that depicted in the above-cited U.S. Pat. No. 5,325,853, the entire contents of which are hereby incorporated by reference for any purpose, employs an array of sensors, typically a bank of aligned sensors on a ceramic chip in a flow-through chamber. The flow-through chamber, as packaged, further contains a calibration medium retained in situ with respect to corresponding sensors to be calibrated such that when the disposable cartridge is activated in conjunction with insertion into and electrical connection with the analytical device, calibration signals are produced by the sensors on the disposable cartridge which enables immediate automatic calibration of the sensors. The sample may thereafter be introduced through an entry port in a manner which causes the calibration medium to be displaced from the flow-through chamber and replaced by the blood or other fluid sample then in direct contact with the sensors. The array of electrochemical sensors then produces electrical signals in accordance with the characteristics of the sample.

The disposable sample cartridge carries a heater in the form of a thin or thick film resistor carried on the sensor chip itself designed to bring the sample quickly to the temperature desired for the analytic determination based on an optical sensor and remote control from within the analytical device. Such a system is depicted in Hieb et al., U.S. Pat. No. 5,232,667, assigned to the same assignee as the present invention, the entire disclosure of which is incorporated herein by reference for any purpose. Once the desired temperature is reached, the electrical signals from the electrochemical sensors are received and processed by the portable analyzer and the results made available on a display and/or in printed form. Other suitable "cartridges" are used in association with the other modules.

It will be appreciated by those skilled in the art that the analytical instrument is required to provide only the signal processing systems for calibration and measurement. The remote temperature sensing and control system provided in the portable instrument, for example, controls only the electric input to a heater located in the disposable cartridge. There is no heating system, per se, in the analytical instrument. The heating control system preferably includes an IR probe or other remote temperature sensing device which is used in association with a programmed control or set point temperature to rapidly establish and maintain the desired temperature in the disposable cartridge. Further details of the temperature control arrangement are contained in the above-referenced patent issued to Hieb et al (U.S. Pat. No. 5,232,667).

In operation, the fully portable analytical instrument is brought to the point of sampling, i.e., the location of the patient. A predetermined number of disposable cartridges are removed from a temperature-stabilized packaging and inserted or plugged into corresponding modules of the analyzer. The instrument is activated; the sensors are calibrated automatically and the calibration electronically compensated with respect to an ensuing set of measurement signals. A sample of interest is obtained from the patient and a portion may immediately be transferred to the sample inlet port of the calibrated sensor system on each disposable cartridge. The sample displaces the calibration medium to a storage chamber and avails the electrochemical sensors for an immediate sensing of the corresponding species of interest in the sample. Other types of sensors including electrochemically active reagent test strips may be exposed to the sample and inserted into a corresponding module.

The user determines the particular needs for testing and determines which modules to attach to the base unit of the immediate response medical analyzer. Plugging the disposable cartridges and inserting relevant sample strips into the respective module of the portable medical analyzer activates the system. The activation of the system also activates the temperature control system which maintains the sensor chip, or equivalent, at the desired calibration and analysis temperature for those determinations that require temperature control. If the sample within the cartridge is at a different temperature, the temperature control system reacts quickly and controls the sensors to restore the desired temperature to the system. Of course, some determinations, including glucose measurement, do not require temperature control.

After the determinations have achieved equilibrium and the corresponding signals have been read by the analyzer, the analyzer computes the results based on the sensor outputs. The results are made immediately available on a combination touch screen LCD display and as a printed record using an integral printer. It is anticipated that the entire operation from first insertion of the cartridges and activation of the system until printout of the results, assuming the immediate availability of the sample, can be achieved in less than three minutes. In addition to the rapid availability, the results are also stored by the device in memory for later retrieval by touch screen, printer or to be sent via a communications port to an external or remote computer or laboratory.

OBJECTS

It is accordingly a principal object of the present invention to provide a portable, rapidly responding, point-of-care medical device having several modules capable of independently determining a plurality of predetermined analytes from a fluid biological sample.

Another object of the present invention is to provide a rapidly responding, portable medical analytical instrument capable of interfacing with several self-contained, self-calibrating, or pre-calibrated, disposable fluid sample devices of varying construction.

Yet another object of the present invention is to provide a portable sophisticated medical analyzer capable of simplistic user friendly operation.

A further object of the invention is to provide a self-contained point-of-care blood analyte analyzer capable of instant activation and almost immediate response in determining a patient's blood pH, $pO_2$, $pCO_2$, $Na^+$, $Ca^{++}$, $K^+$, hematocrit, glucose and other parameters including oxygen saturation, coagulation or hemoglobin fraction.

These and other objects, as well as these and other features and advantages of the present invention will become readily apparent to those skilled in the art from a review of the following detailed description of the illustrated embodiment in conjunction with the accompanying claims and drawings in which like numerals in the several views refer to corresponding parts.

DETAILED DESCRIPTION OF THE PREFERRED EMBODIMENT

Figure 1A:
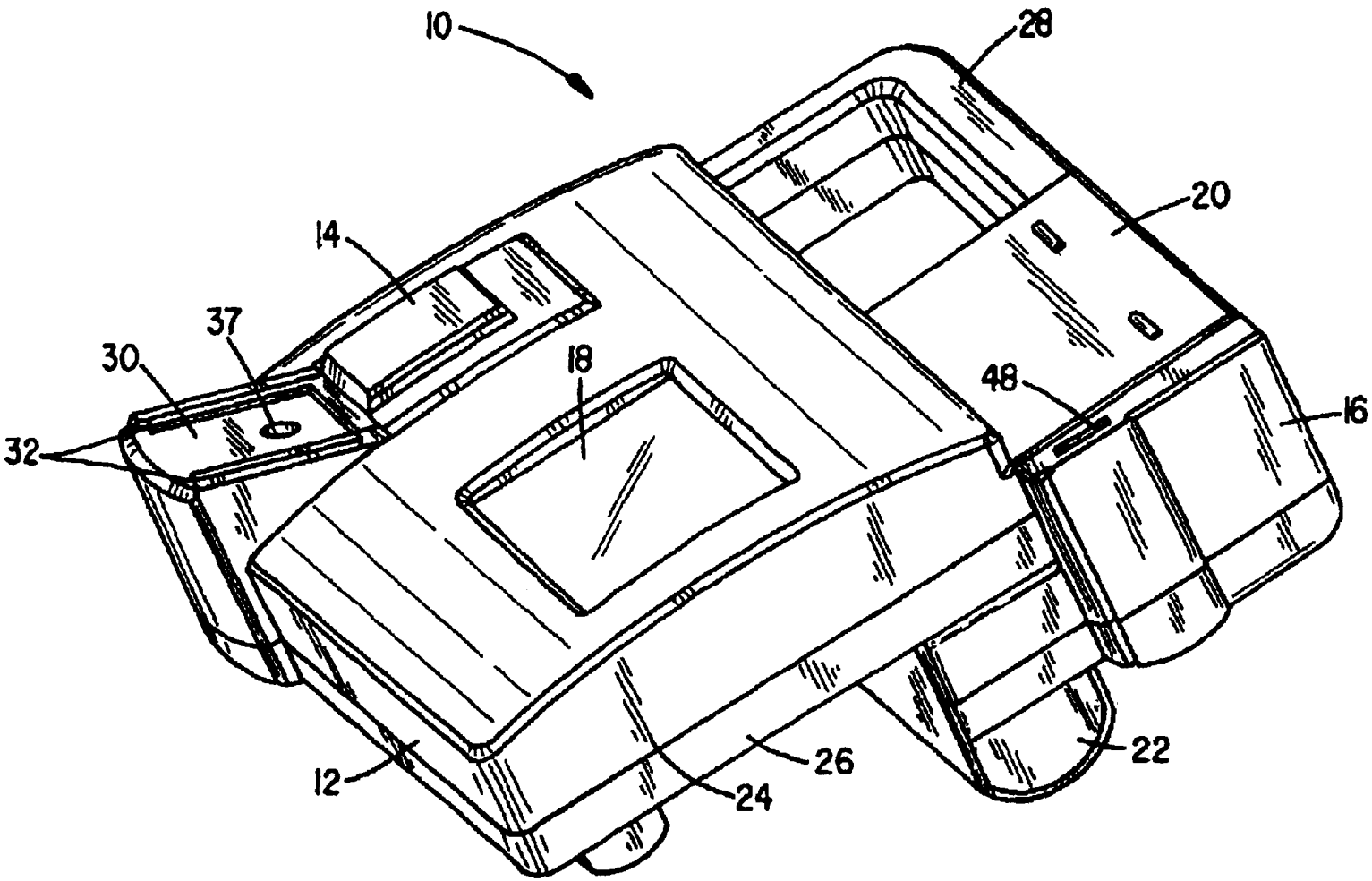
FIG. 1a is a perspective view of the multiple module portable point-of-care analyzer of the present invention.

The present invention includes a point-of-care and immediate response portable medical analyzer that features automated calibration and analysis for a variety of uses. The analyzer includes several interchangeable modules that allow the user to analyze several samples or analyze one sample for several predetermined criteria at the point-of-care without extended delays. Thus blood-gas analysis results can be made available to the attending physician, surgeon, or other health care provider within a minute or two after the drawing of a sample. Moreover, it takes no particular skill to operate the portable medical analyzer inasmuch as both calibration and sample analysis have been automated in conjunction with a unique self-calibrating system. A disposable plug-in cartridge unit interfaces with the medical analyzing device or a reagant strip is automatically interfaced with an output system. While the illustrated embodiments described below are directed to blood-gas and blood-electrolyte analysis, it will occur to those skilled in the art that these are meant as examples and are in no way intended to introduce limitations to the scope of the invention and that the system can be adapted to other analyses involving blood or other body sera without departing from the essential premises of the invention. It will be appreciated from the views of FIGS. 1a–4 that one advantage of the portable analyzer of the invention is that it is mechanically simple and eliminates the need for medical personal to transport samples to a plurality of diagnostic analyzers.

Figure 1B:
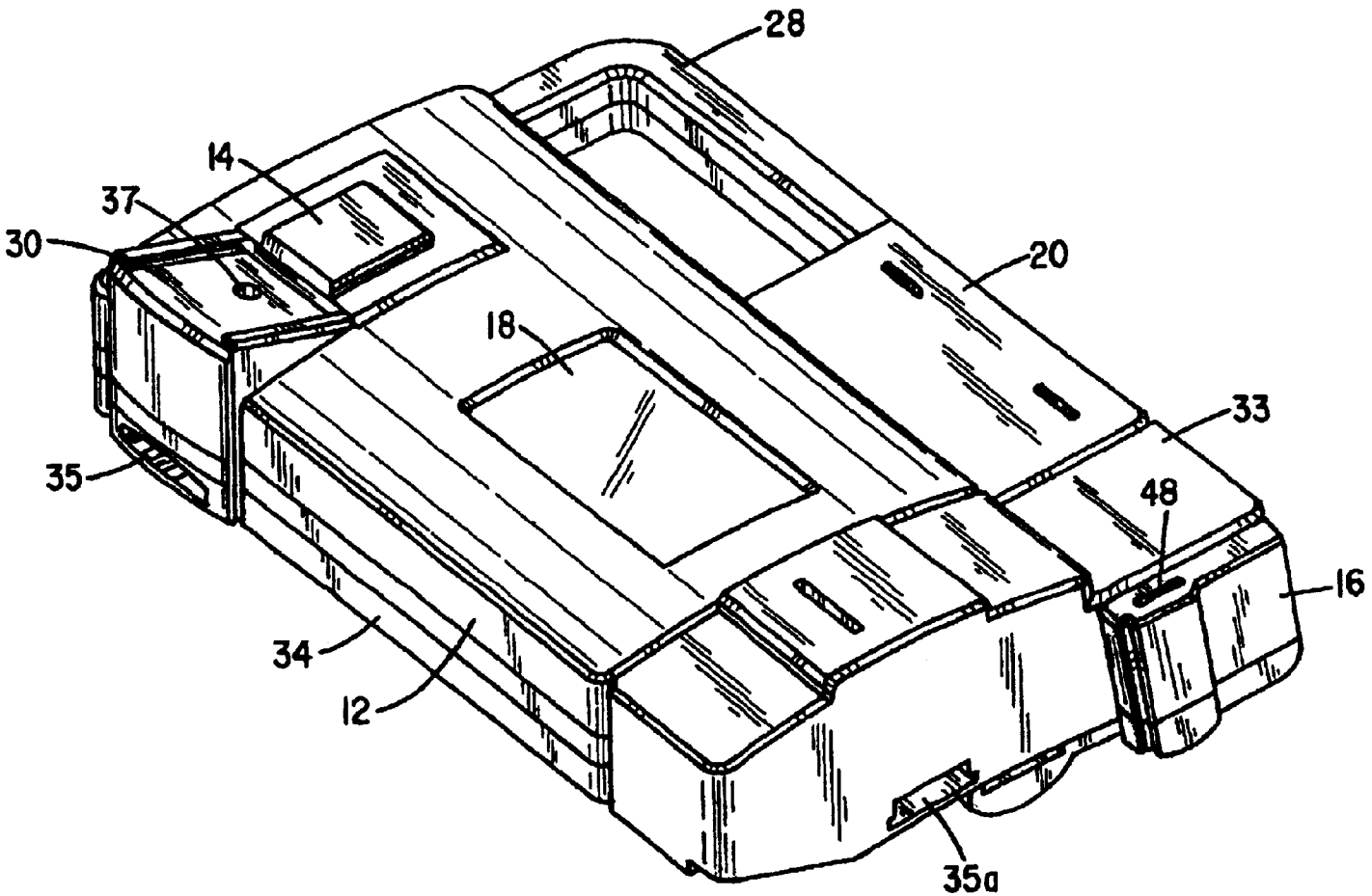
FIG. 1b is a perspective view of a multiple module similar to the analyzer of FIG. 1a with an additional module attached.

With this in mind attention is directed first to FIGS. 1a and 1b where a portable analytic device in accordance with the present invention is shown generally at 10. The base unit device 10 includes a housing 12, a first integrator permanent module 14, a second removable module 16, a touch screen interactive display 18, a printer 20, and a replaceable power supply 22. The base unit enclosed in the housing 12 also includes an upper section 24 and a lower section 26, and includes a void area to define a handle 28. An attached removable second module is shown at 16. The first integrator permanent module 14 includes a cartridge receptacle 30 having a pair of guide flange 32 to hold and guide the sides of a disposable cartridge 140 (see FIG. 8) into the receptacle 30. As shown in FIG. 1b, an additional module 33 may be interposed between the module 16 and the basic analytical device 10. The embodiment of FIG. 1b notably further includes an additional interface section 34 which includes a plug receptacle 35 represents another interface to receive yet another measurement module having an input and output integrated into the basic analytical unit 10.

A remote temperature sensor 36 is positioned in the receptacle 30 (see FIG. 4) beneath an opening 37, thereby providing for temperature measurements of the cartridge 140 as further described below. As best seen in connection with FIG. 4, the interactive display 18 includes a touch screen with an 8×8 grid mask 42 associated with an output LCD window or cover 44 which is fastened beneath an opening 46 in the top housing member 24.

The power supply 22 includes a battery pack, which supplies power through ON-OFF control to the microprocessor, cartridge interface and the touch screen 18. Common voltages are supplied as needed within the processing circuitry through a variety of voltage converters which also supply the liquid crystal display bias and the back lighting for the touch screen 18. This system is considered conventional to those skilled in the art, and further explanation is believed unnecessary.

Module 16 is a glucose meter that includes a receptacle 48 for insertion of a test strip. Without any limitation intended, the module 16 may utilize, for example, the motherboard and test receptacle of a SURESTEP glucose meter available from Lifescan, Inc. Milipitis, Calif. The motherboard and test strip receptacle are mounted to the module and are electrically coupled to a connector that interconnects a communication line and power supply to the internal electrical components contained within housing 12. A relay and control line may be added to allow control of the power supplied to the module 16.

Module 33 may be capable of performing a coagulation assay such as PT (prothrombin time), PTT (activated partial thrombo-plastin time) or ACT (activated clotting time). This module may measure whole blood coagulation time and includes a system for receiving a liquid sample into a reaction chamber containing a reagent material which reacts with the sample to perform the detmination. The reaction can be monitored optically to determine the assay time. Such a system is illustrated and described in U.S. Pat. No. 4,849,340 to Oberhardt, the details of which are deemed incorporated by reference herein for any purpose. The output signals from that module are digitized and processed within the module itself prior to being communicated to the base unit.

Those skilled in the art will appreciate that modules 14, 16 and 33 may represent different modular units of suitable construction modified as needed to interface with electrical components of the present invention. Optionally, additional modular units may be added in stacked or separate arrangements. The appropriate interconnects including communication and power supply links can be provided as direct plug-in linkages from the base unit and through other sensor modules. Without any limitation intended, dedicated removable modular units may include a visible light sensing device that makes co-oximetry measurements such as total hemoglobin concentrations (tHb), oxyhemoglobin ($O_2Hb$), carboxyhemoglobin (COHb) and methemoglobin (MetHb) of a blood sample contained in a cartridge or cuvette may be mounted in a module and interconnected with the present invention. Modules of this type are available from AVOX Systems Incorporated of San Antonio, Tex. Those skilled in the art will appreciate that the mother board and optical bench of such a sensor may be removed and electrically connected within the housing 12 of the analytic device 10. An external connector may be used to interconnect the sensor module's communication lines and power supply to the device 10. A relay with one control line and may be added to allow control over the module by the device 10. Also, the controlling software may be modified to allow control of the module via the device 10.

Figure 2:
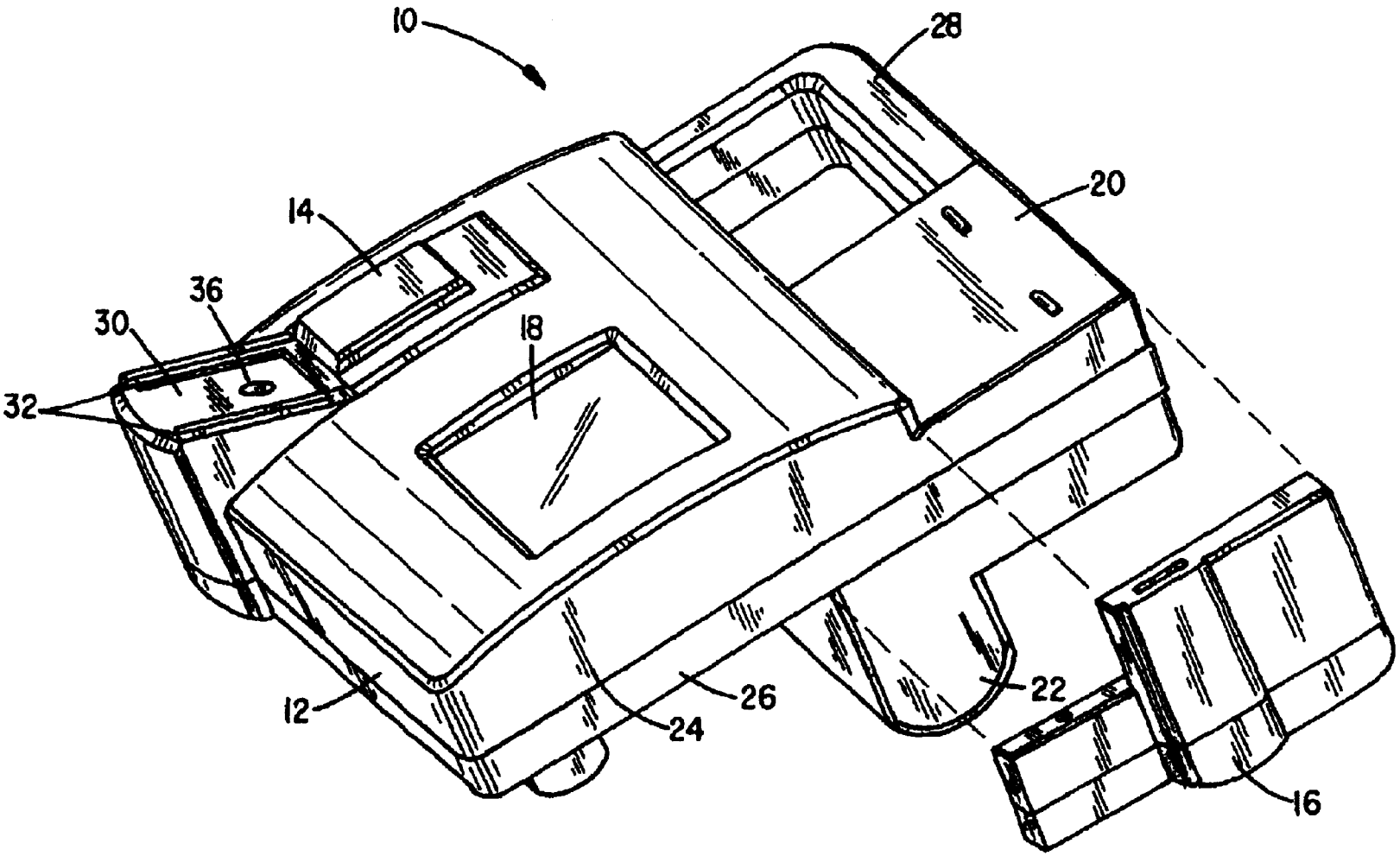
FIG. 2 is a partially exploded perspective view of the device of FIG. 1 showing a module removed.
Figure 3:
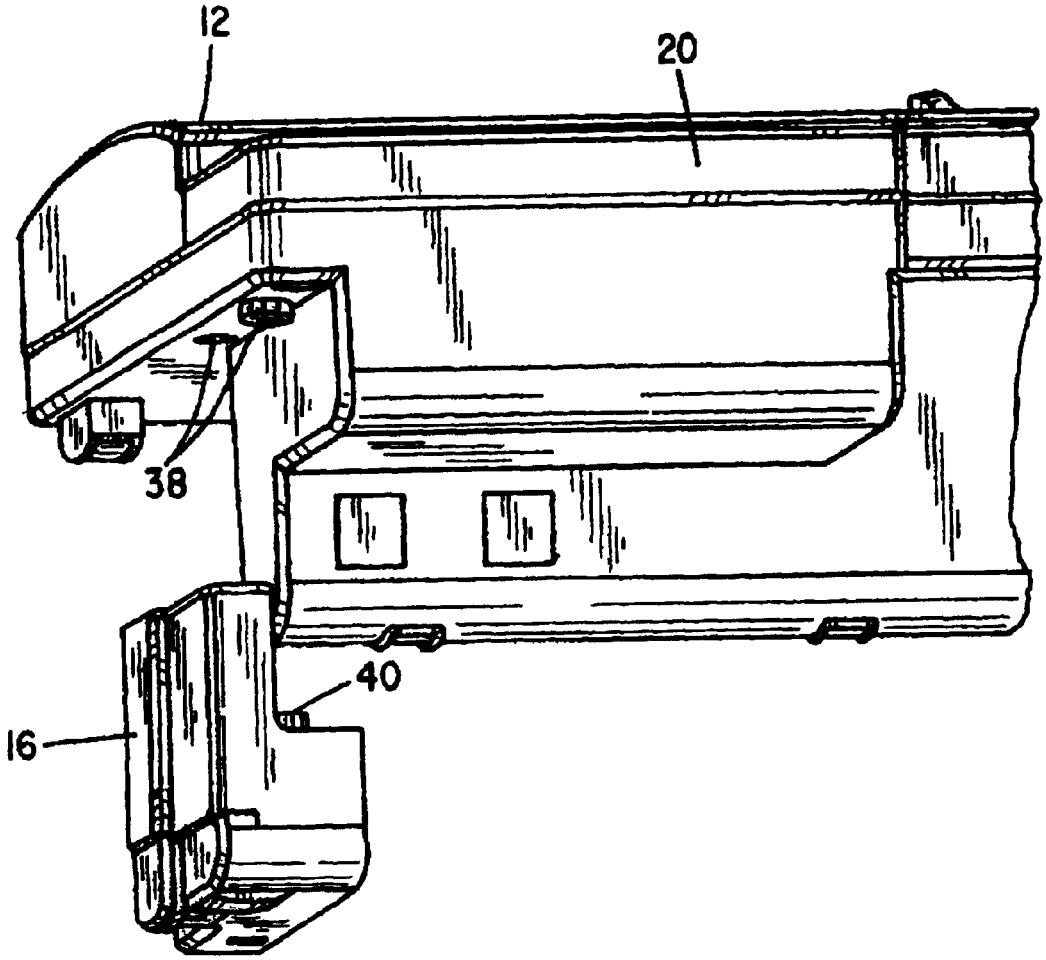
FIG. 3 is a fragmentary, partially exploded, lower perspective view of the device showing a module removed from the analyzer.
Figure 4:
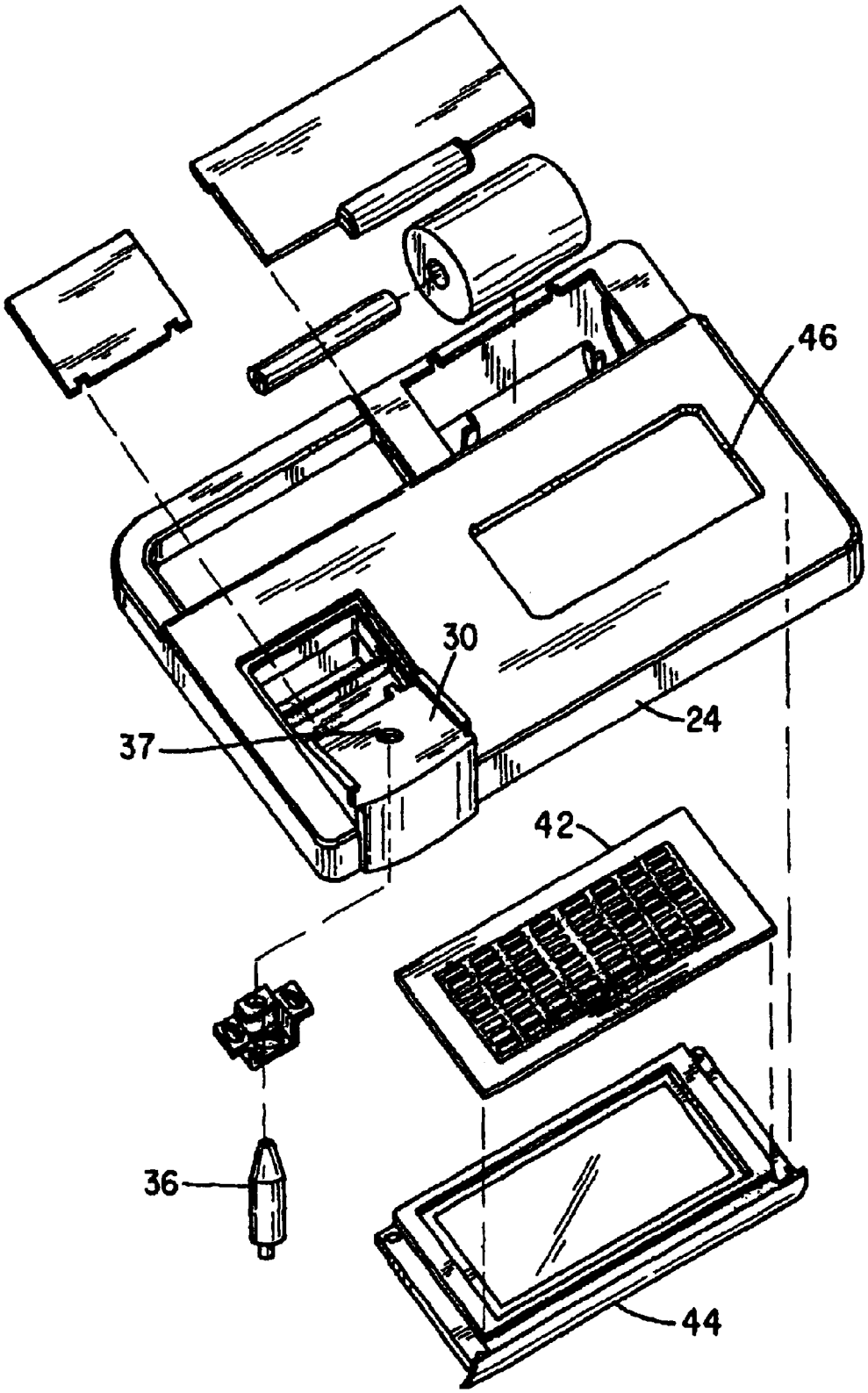
FIG. 4 is a partially exploded perspective view of the top section of the device of FIGS. 1 or 2, without the removed module and including a non-contact temperature sensor probe and print roll.

FIGS. 2 and 3 illustrate the removeability of the second module 16. The module 16 locks onto the housing 12 (FIG. 1a) may utilize a male and female quick release lock of known suitable construction. When the module 16 is locked in place, the electrical contacts 38 of the module engage with the electrical contacts 40 protruding from the housing 12. Those skilled in the art will appreciate that a plurality of electrical contacts may be utilized to form a serial port or other electrical connection of known suitable construction to thereby interconnect the internal electrical components of the module 16 with an integrated circuit and central processing unit (CPU) contained within the housing 12. The module 16 includes a receptacle 48 adapted for receiving a disposable diagnostic test strip or electrochemical sensor of known suitable construction. The module 33 of FIG. 1b attaches to the housing 12 in a similar manner and includes pass-through interfaces and housing lock system to accommodate the module 16 in a piggyback or tandem stacked arrangement. Note that module 33 also has a further plug receptacle 35a situated to accommodate yet annother modular sensor.

Figure 5:
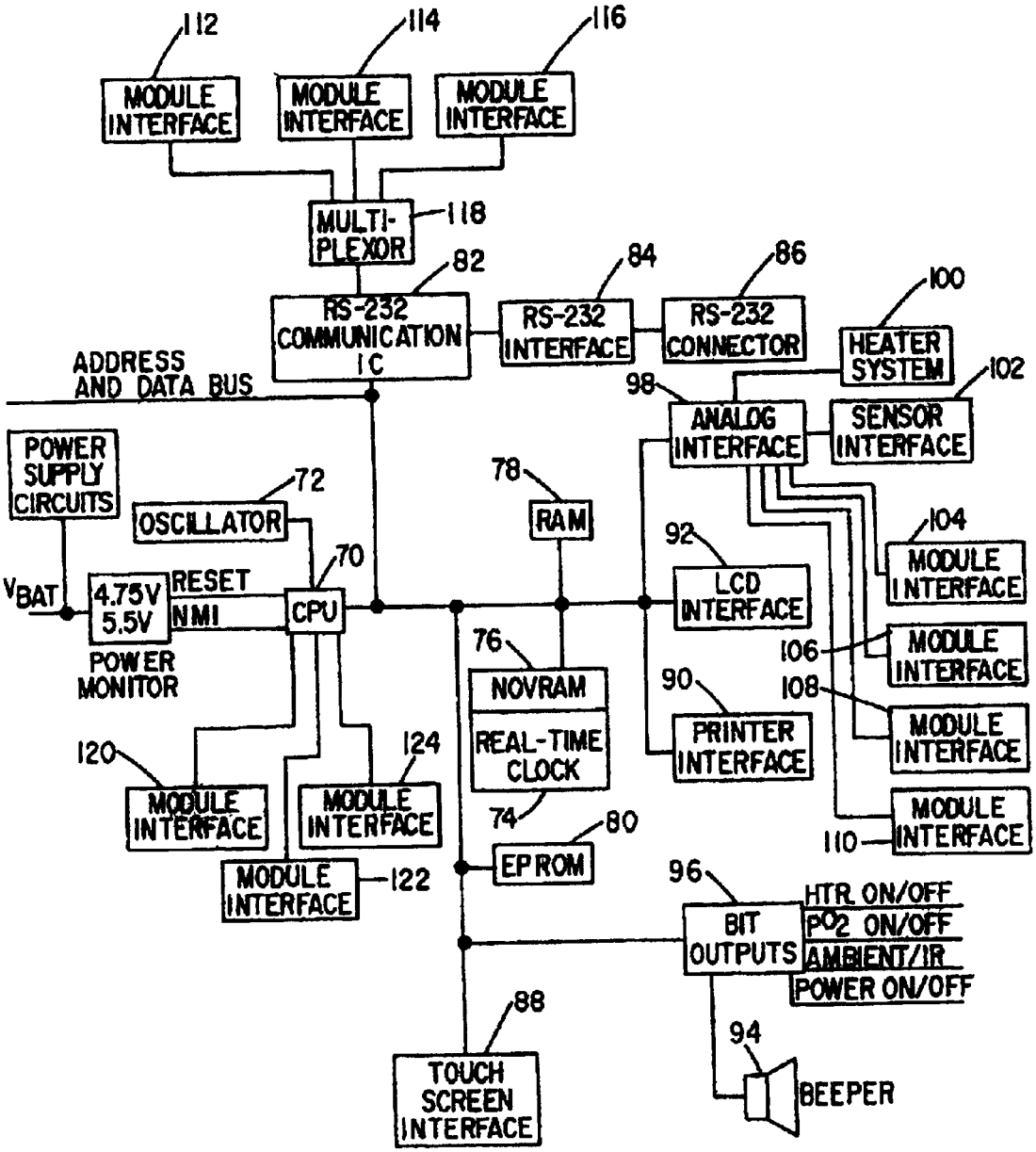
FIG. 5 is a schematic system block diagram for one embodiment of the multi-module or multiple module portable medical analyzer of the invention.
Figure 6:
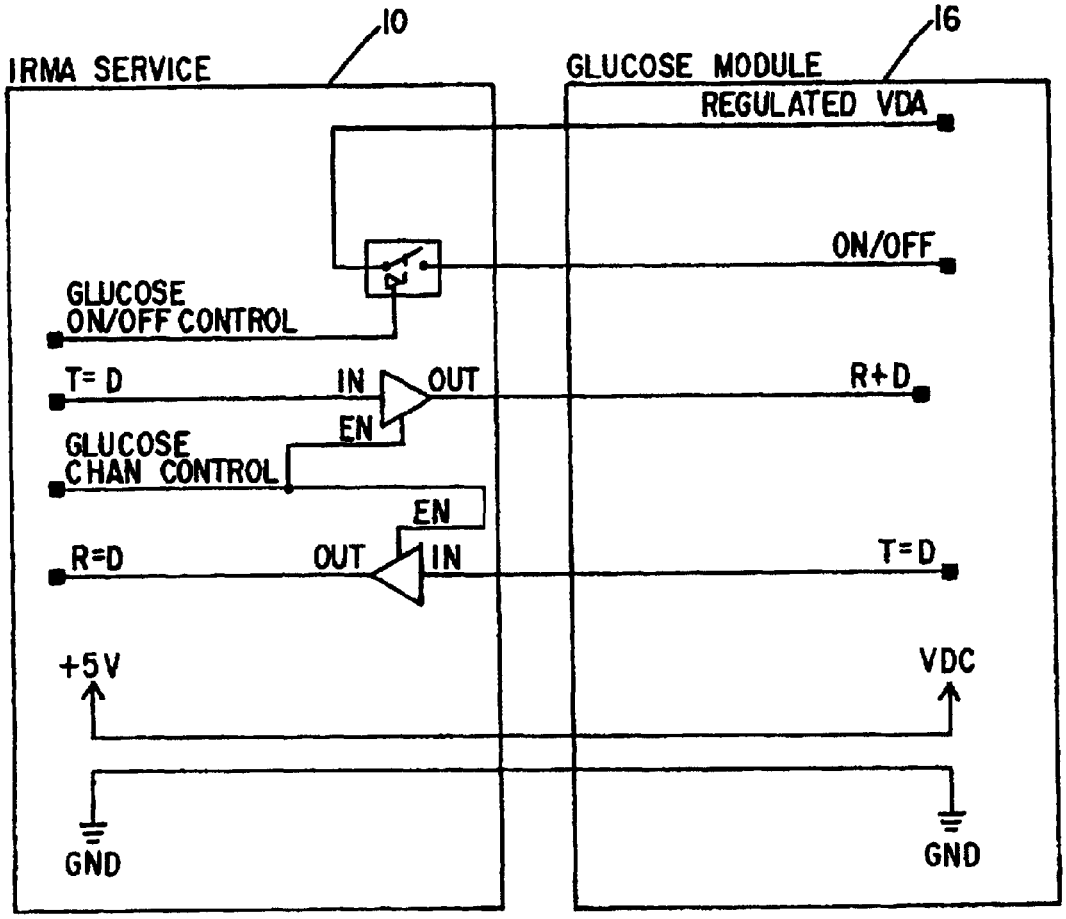
FIG. 6 is an electrical schematic illustrating the connection between a glucose module and the integrated circuit of the analyzer.
Figure 8:
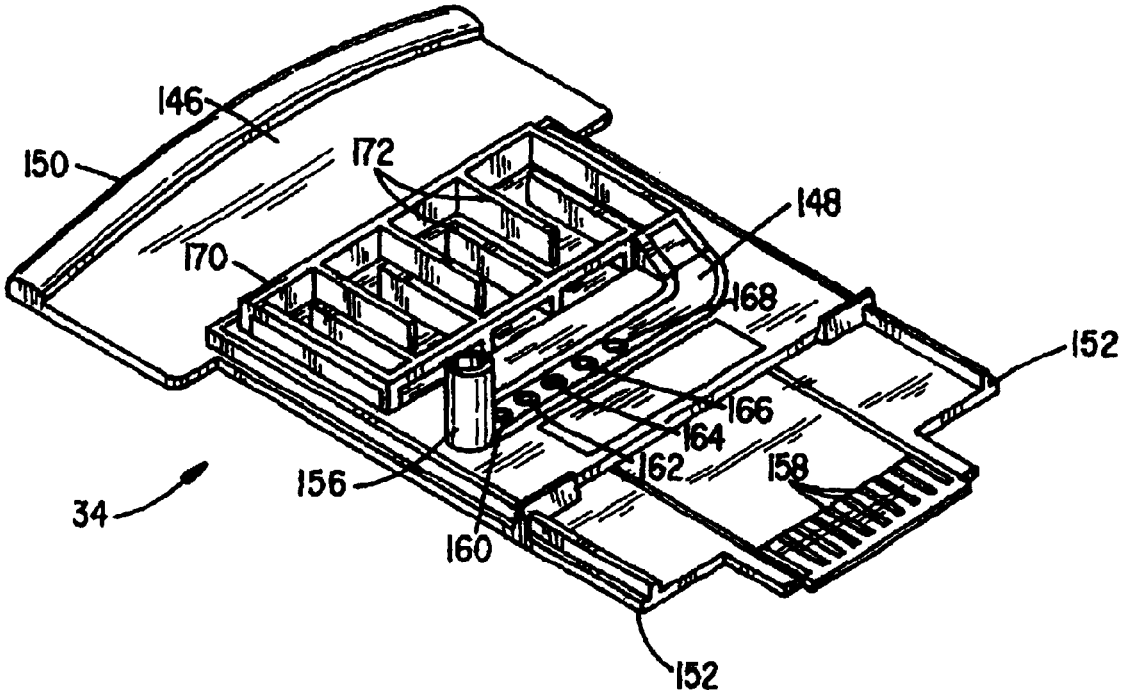
FIG. 8 is a perspective view of a disposable cartridge for use with the analyzer of the invention.
Figure 9:
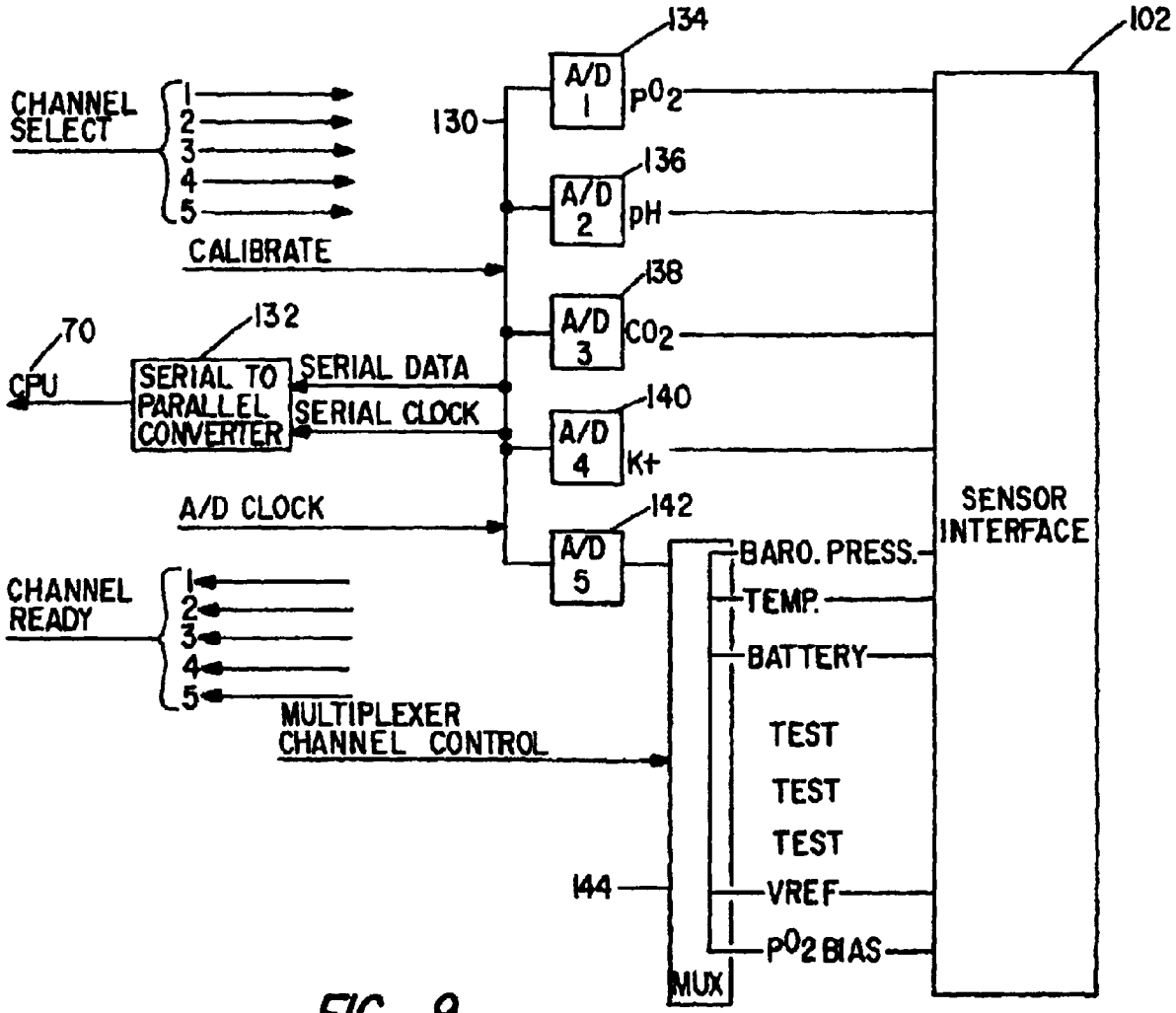
FIG. 9 is a schematic diagram of an analog interface subsystem associated with FIG. 5.

In accordance with the operation of the portable medical analyzer of the invention, a typical operating system is shown in block diagram in FIG. 5. Additional details of subsystems are illustrated in FIGS. 6 and 9. The interface of module 16 with the integrated circuit contained within housing 12 is depicted in FIG. 6 and the analog interface system is depicted in FIG. 8.

Additional information can be gleaned with reference to the schematic block diagram of FIG. 5. The system is operated by a programmed central processing unit 70 which operates in conjunction with a voltage controlled oscillator 72, real-time clock 74 with associated non-volatile random access memory (novram) 76 random access memory (RAM) 78 and erasable programmable read only memory (EPROM) 80. The system further includes a communication integrated circuit 82 (RS232 with interface 84 and a typical circuit connector 86). Also included is an interface 88 for the interactive touch screen display 18. A printer interface 90 for printer output and LCD interface 92 are also shown. Various switches and an alarm or beeper device 94 are connected through a bit output device at 96. An analog interface 98 interconnects the heater system 100, sensor interface 102 and module interfaces 104–110. Those skilled in the art will appreciate that additional module interfaces 112–116 may be interconnected with integrated circuit 82 via a multiplexor 118. Additionally, module interfaces 120–124 may be directly connected to the central processing unit 70. In this manner, those skilled in the art will appreciate that a variety of modules having various processing components may be rendered compatible with the present portable device 10.

Figure 11:
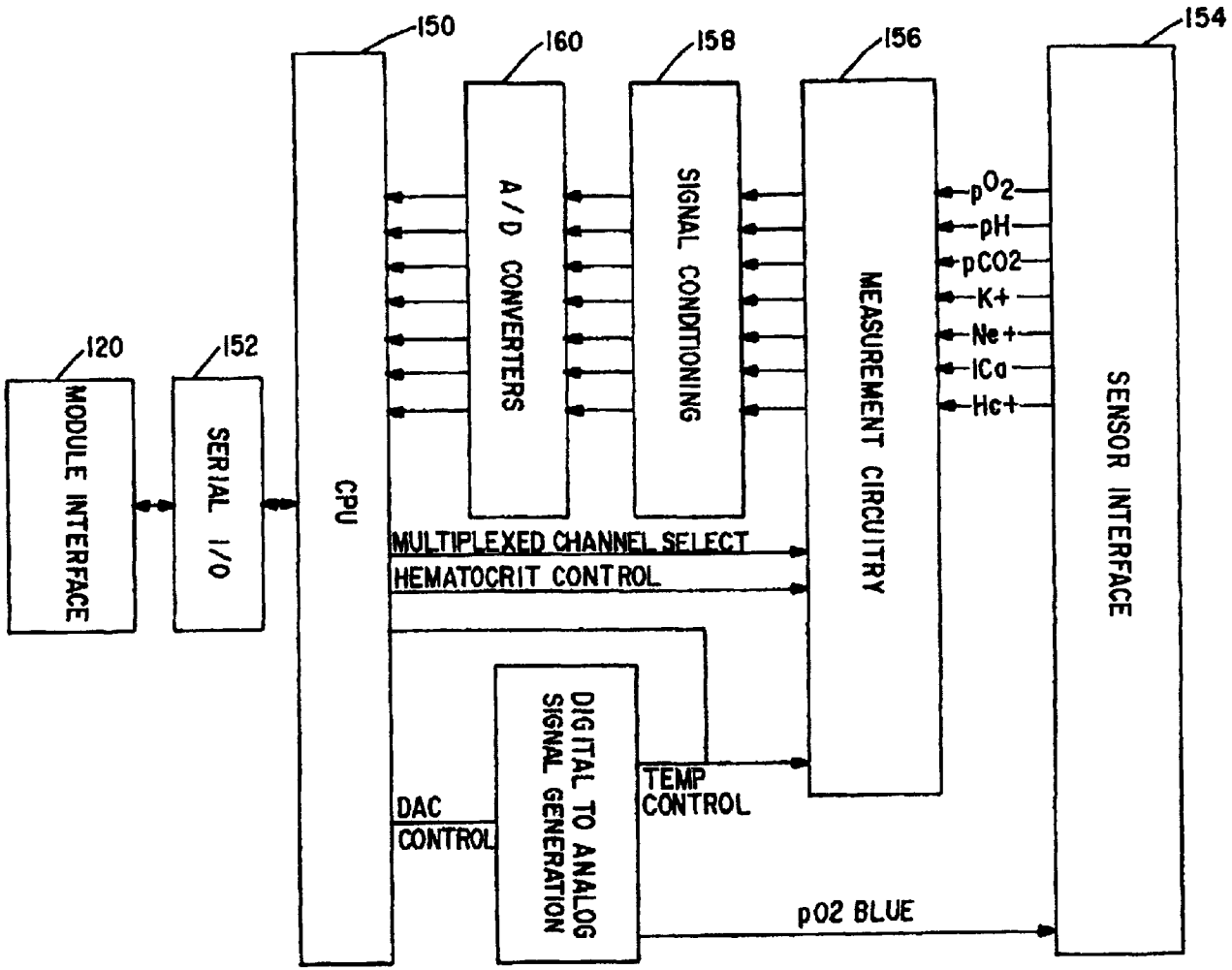
FIGS. 11–13 depict schematic block diagrams of examples of modules that interface with each of the modular interface system types depicted in FIG. 5.
Figure 12:
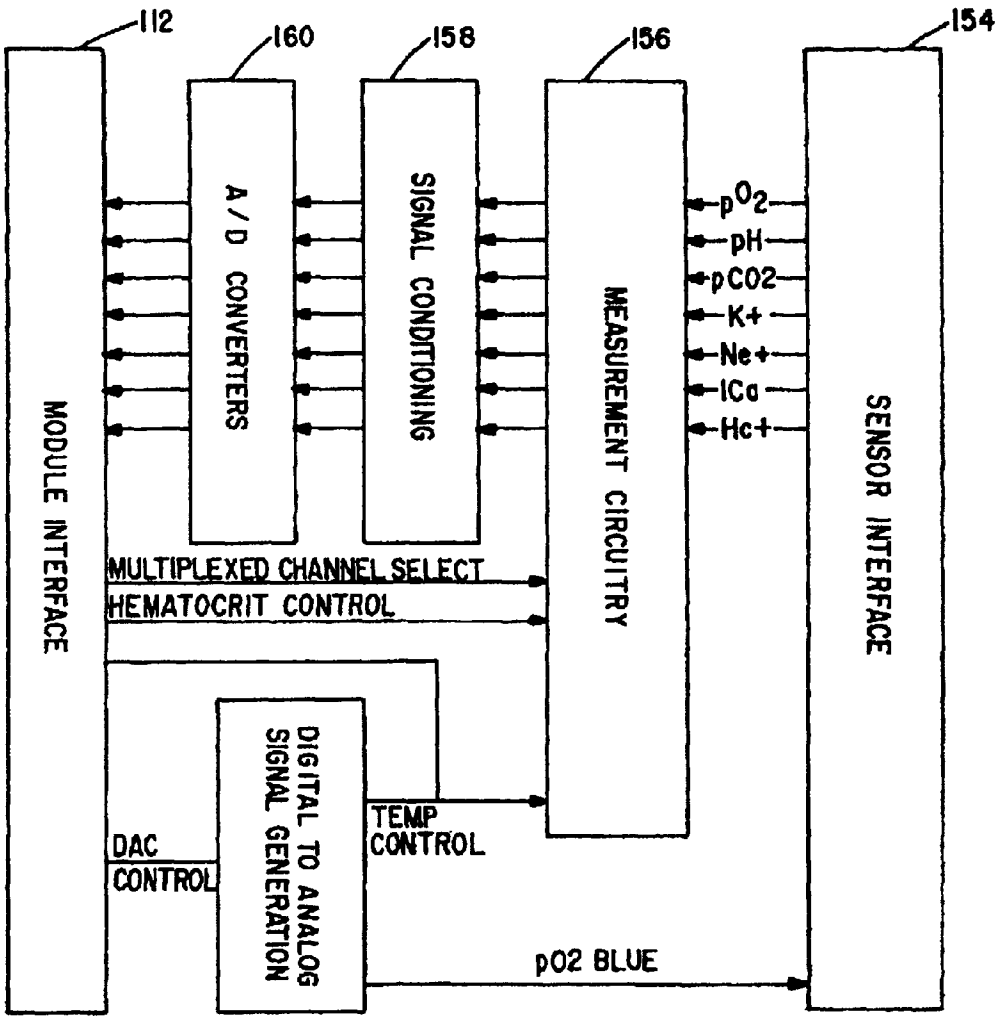
Figure 13:
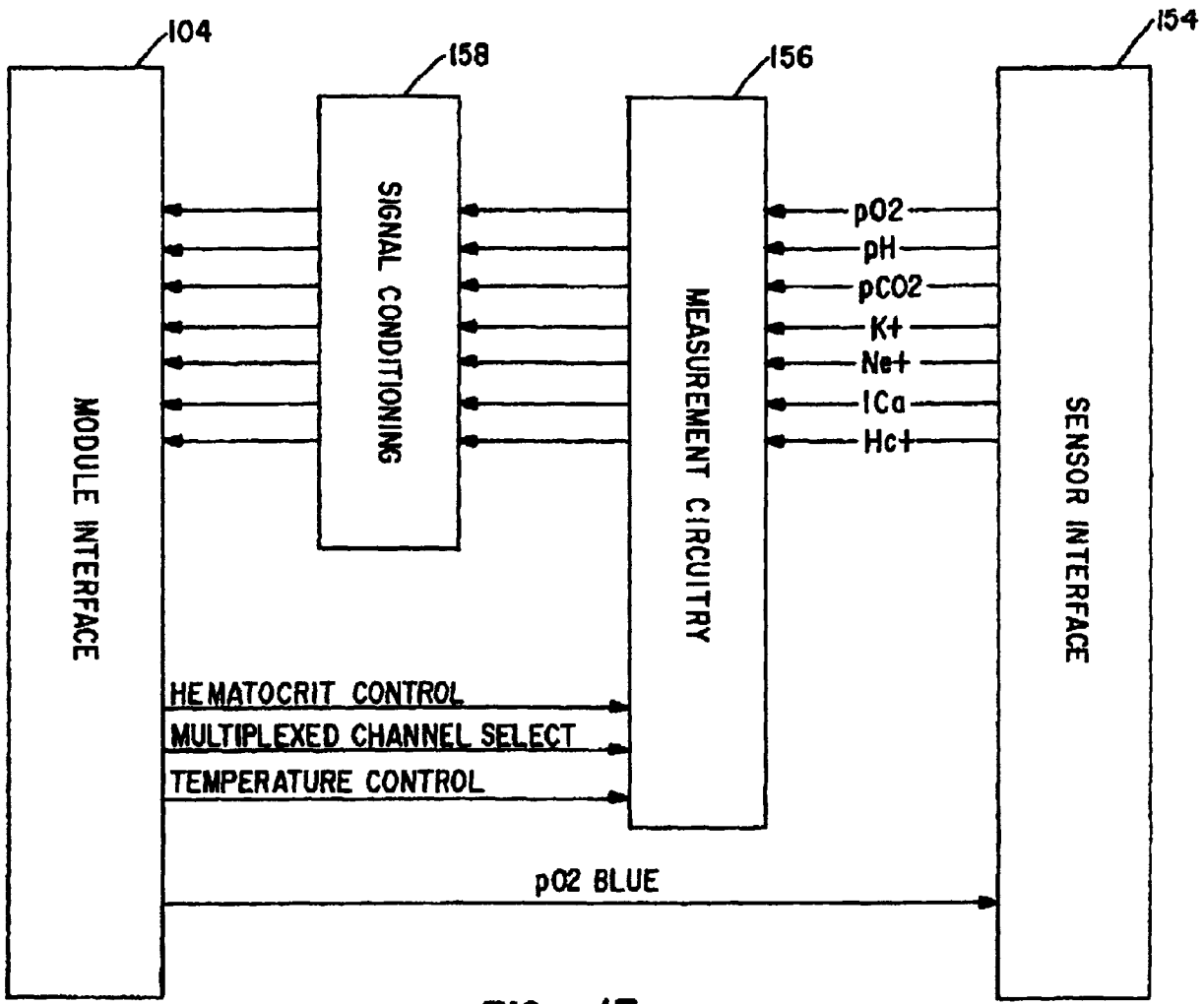

For example, FIG. 6 shows a glucose measuring module of common known construction electrically coupled to an immediate response medical analyzer (IRMA). FIG. 11 depicts a typical module of a class designed to interface with the instrument 10 through any of interface modules and may include a CPU 150 connected to the module interface through a serial input/output device. The module further typically includes a sensor interface 154 with associated measurement circuitry 156 signal conditioning system 158 and A/D signal converter 160. A CPU controlled DAC signal generator 162 provides an analog interface with a temperature control system and sensor interface 154. The module depicted in FIG. 12 is of a class that are designed to connect to a module interface through a multiplexer and communication IC as at 118 and 82. This includes any of the module interfaces 112, 116. It will be appreciated that the modules 16 and 33 are compatable with this type of interface. FIG. 13 depicts yet another type of connected device compatable with the module interfaces 104–110.

With respect to FIG. 9, it will be appreciated that once the disposable cartridge is plugged into the analyzer and the analyzer is turned on, calibration signals are almost immediately available on a clock controlled or prioritized channel selective interface bus as at 130 such that by employing a serial clock, the serially obtained data available on the bus 130 can be processed by a serial to parallel converter 132 interfacing with the central processing unit 70 to sort out the multiple signals being received from A-to-D converters 134–142. Corrective data where applicable and reference measurements are provided via the A-to-D converter 142 from a multiplexer channel control 144 that receives input from a variety of sources including barometric pressure sensor, temperature, reference electrode signals and an oxygen bias signal, if used, from the sensor interface 102. The clock controlled CPU interfaces with both the multiplexer channel control and the remaining electrochemical sensors via the serial to parallel converter in a manner which uses the signals together with the available calibration condition data from the multiplexer via A-to-D converter 142 to accurately calibrate each of the species sensors for subsequent use in making a determination in the sample.

It will be appreciated that in this manner, each disposable cartridge is automatically individually calibrated with respect to the measurements to be made once connected to the analyzer and activated. Determination of each sample is then made pursuant to an individualized calibration based on the disposable cartridge itself and not based on calibration of any of the components in the portable analytical device.

Figure 7:
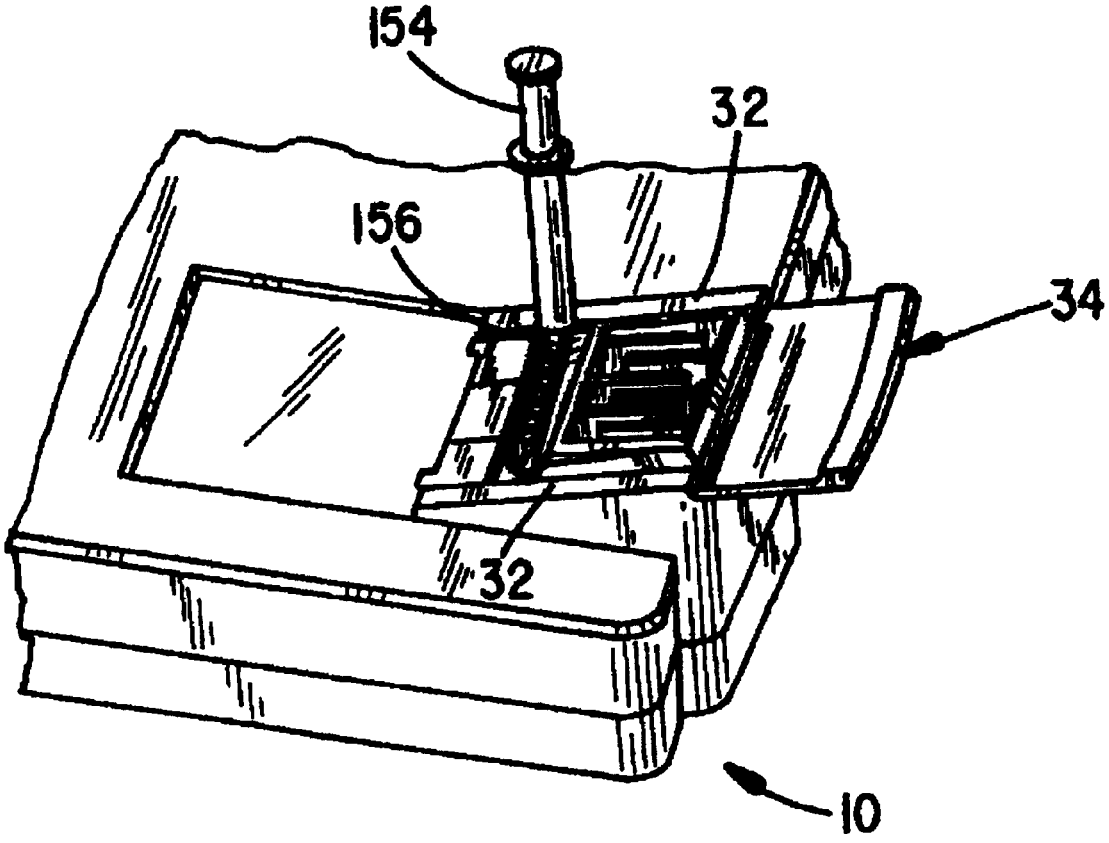
FIG. 7 is a fragmentary perspective view of a cartridge receptacle interface with a cartridge inserted.

FIG. 8 depicts a perspective view of the disposable cartridge 34 designed for use in association with the medical analyzer 10 of the invention. The cartridge 34 includes a substantially planar base member or plate 146 and a housing 148 fixed to the base member 146. One end of the cartridge is formed to include a handle with a gripping flange 150 to obtain a better grasp of the cartridge 34. Side flange members 152 extend from the sides of the planar base and slide under guide flanges 32 of the cartridge receptacle 30. FIG. 7 shows the cartridge 34 aligned and engaged with receptacle 30 and having an injection syringe 154 positioned to introduce a sample into a sample port 156.

The cartridge is further provided with an array of electrical leads or terminals as at 158 configured to connect with corresponding terminals in the analytical instrument cooperating in the exchange of electrical signals between the analytical instrument and cartridge in a well-known manner. These terminals connect to corresponding conductors (not shown) of the receptacle 30 which provide all necessary input and output connections to control the functions and transmit the necessary signals between the cartridge and the analytical instrument. The cartridge housing 148 further defines a flow-through analytical cell chamber or volume containing an array of electrochemical sensors 160–168 connected to a relatively larger waste receptacle chamber 170. The cartridge waste volume 170 includes a retention maze in the form of a plurality of partitions as at 172. As recognized above, the cartridge and module 14 are described in greater detail in U.S. Pat. No. 5,325,853, the entire disclosure of which has been incorporated herein by reference.

Figure 10:
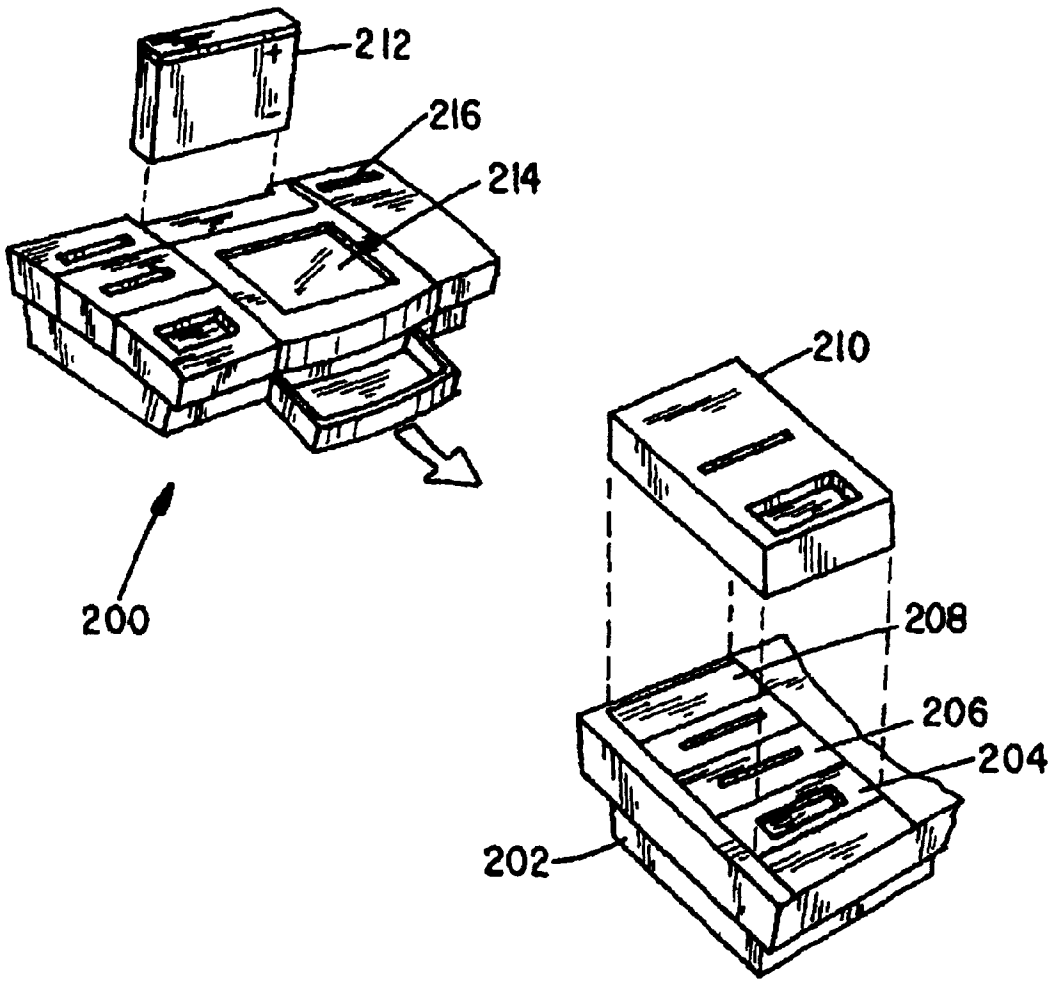
FIG. 10 is a partially exploded perspective view of an alternate embodiment of the portable point-of-care analyzer of the present invention.

An alternate embodiment of the portable device 10 is shown generally at 200 in FIG. 10. The device is adapted for receiving a cassette 202 in which is electrically integrated a plurality of testing modules 204–208. The cassette 202 is provided with a cover that engages with the base of cassette 202. A rechargeable, replaceable battery pack 212 is shown elevated above the portable device 200. The device 200 also includes an interactive display 214 and printer 216. The cassette 202 includes electrical connectors that electrically interconnect each module 204–208 with the electrical components contained within the device 200 (including a central processing unit and integrated circuit). The modules 204–208 may be removed from the cassette 202 and are interchangeable. In this manner, the user may either analyze several samples using similar modules or may select different modules to perform varying analysis and diagnostics of a single sample.

This invention has been described herein in considerable detail in order to comply with the Patent Statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

What is claimed is:

1. A portable point of care medical analyzer that enables an operator to rapidly obtain results for a plurality of diverse analyses, said analyzer comprising:

(a) a base unit having a main CPU and including signal processing devices and circuitry for rapid processing of electrical signals generated by electrical, electrochemical, optical or mechanical sensors of one or more associated analytical modules;

(b) at least one permanent analytical module integral with said base unit which [includes a disposable] *is adapted to receive a removable* test device having electrochemical sensors for making [a plurality of] determinations characteristic of a fluid [serum] sample *selected from blood or other body fluid*;

(c) one or more types of module interface units for connecting and interfacing between one or more removable analytical module units and said base unit;

(d) one or more [dedicated] removable analytical module units for making specific determinations and which are designed to be plugged into said base unit and connect electrically to a specific type of modular interface unit;

(e) wherein the combination of said base unit signal processing devices and circuitry and said module interface units enables direct utilization of the output signals from each of said removable modules; and (f) [common output devices in said base unit for providing visual or printed display of determinations from all modules.] *the base unit including programming logic and circuitry for receiving signals from said permanent analytical module and one or more of said removable analytical modules and directing an analytical information output.*

2. The [device] *analyzer* of claim 1 wherein at least one of said removable analytical module[s also] *units is a module that* makes a determination which utilizes a [disposable] test device *that can be removed from the at least one of said removable modules*.

3. The [device] *analyzer* of claim 2 wherein said [disposable] *at least one of said removable module units that makes a determination which utilizes a* test device *that can be removed from the at least one of said removable module units* is a *removable module that uses a* test strip.

[4. The device of claim 3 wherein said test strip is used in a glucose meter.]

5. The [device] *analyzer* of claim 2 wherein said one or more removable analytical module[s] *units* include a glucose meter.

6. The [device] *analyzer* of claim 1 wherein at least one *or more types of* module interface unit*s include a unit which* is connected to a communications IC.

7. The [device] *analyzer* of claim 6 wherein said one or more removable analytical module[s] *units* include a glucose meter.

8. The [device] *analyzer* of claim 6 wherein said one or more removable analytical module[s] *units* include a prothrombic time assay module for performing general coagulation measurements.

9. The [device] *analyzer* of claim 6 including a plurality of module interface units connected through a multiplexer to said communications IC.

10. The [device] *analyzer* of claim 1 wherein at least one module interface unit is connected directly with said main CPU of said base unit.

11. The [device] *analyzer* of claim 1 wherein at least one module interface unit is connected to said main CPU of said base unit through an analog interface.

12. The [device] *analyzer* of claim 1 wherein said one or more removable analytical module[s] *units* include a module *unit* for performing general coagulation measurements.

13. The [device] *analyzer* of claim 12 wherein said *module unit for performing general coagulation measurements performs at least one measurement from* general coagulation measurements [include] *including* prothrombin time (PT), activated partial thrombo-plastin time (PTT) and activated clotting time (ACT) *measurements*.

14. The [device] *analyzer* of claim 11 wherein said one or more [dedicated] removable analytical module[s] *units* includes a visible fight sensing device that makes co-oximetry measurements.

15. The [device] *analyzer* of claim 14 wherein said *device that makes cooximetry measurements is a device that can make* co-oximetry measurements *that* include total homoglobin concentrations (tHb), oxyhemoglobin ($O_2H$[B]*Q*) *measurements*, carboxyhemoglobin (COHb) *measurements* and methemoglobin (MetHb) *measurements*.

16. A portable point of care medical analyzer that enables an operator to rapidly obtain results for a plurality of diverse analyses, said analyzer comprising:

(a) a base unit having a main CPU and including signal processing devices and circuitry for rapid processing of electrical signals generated by electrical, electrochemical, optical or mechanical sensors of one or more associated analytical modules;

(b) at least one permanent analytical module integral with said base unit [including a disposable] *which uses a removable* test cartridge having electrochemical sensors for making [a plurality of] determinations characteristic of a fluid [serum] sample *selected from blood or other body fluids*;

(c) one or more types of module interface units for connecting and interfacing between one or more removable analytical module units and said base unit;

(d) one or more [dedicated] removable analytical module units for making specific determinations and which are designed to plug into said base unit and connect electrically to a specific type of modular interface unit;

(e) wherein the combination of said base unit signal processing devices and circuitry and said module interface unit enables direct utilization of the output signals from each of said removable modules;

(f) [common output devices in said base unit for providing visual or printed display of determinations from all modules; and] *the base unit including programming logic and circuitry for receiving signals from said permanent analytical module and one or more of said removable analytical modules and directing an analytical information output; and,*

(g) wherein at least one removable analytical module is designed to attach to another removable analytical module in a stacked arrangement in a manner such that both removable modules connect to a module interface unit.

17. The [device] *analyzer* of claim 16 wherein at least one module interface unit is connected through a multiplexer to a communications IC.

18. The [device] *analyzer* of claim 16 wherein at least one module interface unit is connected directly with said main CPU of said base unit.

19. The [device] *analyzer* of claim 16 wherein at least one module interface unit is connected to said main CPU of said base unit through an analog interface.

20. The [device] *analyzer* of claim 16 wherein said one or more removable analytical module[s] *units* include a glucose meter.

21. The [device] *analyzer* of claim 16 comprising a removable glucose meter mounted from a prothrombic time assay module.

*22. The analyzer according to claim 1 including a display for displaying determinations from the analytical module units.*

*23. The analyzer according to claim 22 wherein the display is a video display.*

*24. The analyzer according to claim 23 wherein the video display is mounted in the base unit.*

*25. The analyzer according to claim 23 wherein the video display is an interactive display including a touch screen.*

*26. The analyzer according to claim 22 wherein the display is a printer.*

*27. The analyzer according to claim 26 wherein the printer is mounted in the base unit.*

*28. The analyzer according to claim 22 wherein the display includes both a printer and a video display.*

*29. The analyzer according to claim 28 wherein both the printer and the video display are mounted in the base unit.*

*30. The analyzer according to claim 1 including a communication port for sending results to an external or remote computer.*

*31. The analyzer according to claim 1 including no heating system, per se, in the base unit.*

*32. A portable medical analyzer comprising:*

*(a) a base unit having a main CPU and including signal processing devices and circuitry for processing of electrical signals generated by electrical, electrochemical, optical or mechanical sensors positioned in one or more associated analytical modules;*

*(b) one or more module interface units for connecting and interfacing between one or more analytical module units and said base unit;*

*(c) at least one permanent analytical module integral with said base unit which is adapted to receive a removable test device having electrical, electrochemical, optical or mechanical sensors for making determinations characteristic of a fluid sample selected from blood or other body fluid;*

*(d) the base unit being adapted to receive at least one removable analytical module unit for making analytical determinations of blood or other body fluid; and to connect, through a module interface unit, to the at least one removable analytical module; and*

*(e) the base unit including programming logic and circuitry for receiving signals from the at least one removable analytical module unit, when attached thereto, and also from the permanent analytical module, and directing an analytical output.*

*33. A portable medical analyzer according to claim 32 including:*

*(a) a removable analytical module mounted thereon;*

*(i) the removable analytical module mounted on the base unit being configured to make determinations characteristic of a fluid sample selected from blood or other body fluid.*

*34. A portable medical analyzer according to claim 33 wherein:*

*(a) the analytical module permanently mounted on the base unit includes a cartridge receptacle having a pair of guide flanges to hold, in use, a removable sample cartridge.*

*35. A portable medical analyzer according to claim 32 wherein:*

*(a) the base unit includes a temperature sensing device positioned to determine a temperature corresponding to a sample temperature in a removable sample cartridge, when the removable sample cartridge is mounted in the analytical module permanently mounted on the base unit.*

*36. A portable medical analyzer according to claim 32 wherein:*

*(a) the base unit includes a heating control system and programming, to selectively control a temperature of a sample included in a removable sample cartridge, when the removable sample cartridge is mounted in the analytical module permanently mounted on the base unit.*

*37. A portable medical analyzer according to claim 32 wherein:*

*(a) the analyzer includes programming logic for operating the permanent analytical module in both a calibration mode and sample determination mode.*

*38. A portable medical analyzer according to claim 32 including a display for displaying determinations from the analytical modules.*

*39. A portable medical analyzer according to claim 38 wherein the display is a video display.*

*40. A portable medical analyzer according to claim 39 wherein the video display is mounted in the base unit.*

*41. A portable medical analyzer according to claim 39 wherein the video display is an interactive display including a touch screen.*

*42. A portable medical analyzer according to claim 38 wherein the display is a touch screen.*

*43. A portable medical analyzer according to claim 42 further comprising a printer mounted in the base unit.*

*44. A portable medical analyzer of claim 32 including a removable analytical module mounted on the base unit which is configured for performing general coagulation of a blood sample.*

*45. A portable medical analyzer of claim 44 wherein the module for performing general coagulation measurements is configured to perform at least one measurement from general coagulation measurements including prothrombin time (PT), activated partial thrombotlastin time (PTT) and activated clotting time (ACT) measurements.*

*46. A portable medical analyzer of claim 32 including a removable analytical module having a visible light sensing device that makes co-oximetry measurements.*

*47. A portable medical analyzer of claim 46 wherein the device that makes co-oximetry measurements is a device that can make co-oximetry measurements that include total hemoglobin concentrations (tHb), oxyhemoglobin ($O_2Hb$) measurements, carboxyhemoglobin (COHb) measurements and methemoglobin (MetHb) measurements.*

*48. A portable medical analyzer of claim 32 including a removable analytical module comprising a glucose meter.*

*49. A portable medical analyzer according to claim 32 including:*

*(a) a cassette removably engaged with the base unit, the cassette including at least two analytical testing modules;*

*(i) each one of two testing modules included in the cassette being operatively coupled to the base unit.*

*50. A portable medical analyzer according to claim 49 wherein:*

*(a) each module included in the cassette is removably mounted in the cassette.*

*51. A portable medical analyzer according to claim 32 including:*

*(a) a removable and replaceable power supply, including a battery pack, mounted on the base unit.*

*52. A portable medical analyzer according to claim 32 including:*

*(a) a communication link for communicating analytical information from the base unit to a remote computer.*

*53. A portable medical analyzer comprising:*

*(a) a base unit having a main CPU and circuitry to process electrical signals received from electrical, electrochemical, optical or mechanical sensors of at least two associated analytical modules if and when one or more of the at least two analytical modules is operated to evaluate blood or other body fluid removed from a patient;*

*(b) one or more module interface units for connecting and interfacing between the base unit and at least two non-disposable analytical modules capable of making determinations characteristic of fluid selected from blood or other body fluid removed from a patient and presented to the analytical modules via one or more disposable test units;*

*(c) the base unit including programming logic and circuitry for receiving signals from at least two analytical modules, operated to evaluate blood or other body fluid removed from a patient in selected use, and directing an analytical information output;*

*(d) wherein the combination of the base unit and the module interface units enables utilization of output signals from at least two associated analytical modules, in selected operation to evaluate blood or other body fluid removed from a patient.*

*54. A portable medical analyzer according to claim 53 including:*

*(a) an analytical module mounted thereon;*

*(i) the analytical module mounted on the base unit being configured to make determinations characteristic of a fluid sample selected from blood or other body fluid removed from a patient.*

*55. A portable medical analyzer according to claim 53 including:*

*(a) two analytical modules connected thereto;*

*(i) at least one of the two analytical modules being removably mounted on the medical analyzer;*

*(ii) each one of the two analytical modules being configured to make determinations characteristic of a fluid sample selected from blood or other body fluid removed from a patient.*

*56. A portable medical analyzer according to claim 55 wherein:*

*(a) the base unit, one or more module interface units and two analytical modules are configured for selected simultaneous operation of the two analytical modules to provide output signals to the base unit.*

*57. A portable medical analyzer according to claim 55 wherein:*

*(a) the two analytical modules are configured to make different determinations from one another, each of which is characteristic of blood or other body fluid removed from a patient.*

*58. A portable medical analyzer according to claim 53 including:*

*(a) a first analytical module attached thereto;*

*(i) the first analytical module being configured to make determinations characteristic of a fluid sample selected from blood or other body fluid removed from a patient;*

*(b) a second analytical module connected to the base unit which is adapted to receive a glucose test strip, to make a glucose determination of blood.*

*59. A portable medical analyzer according to claim 53 including:*

*(a) a first analytical module attached thereto;*

*(i) the first analytical module being configured to make determinations characteristic of a fluid sample selected from blood or other body fluid removed from a patient; and,*

*(b) a removable second analytical module.*

*60. A portable medical analyzer according to claim 53 including:*

*(a) a display for displaying determinations made from one or more analytical modules.*

*61. A portable medical analyzer according to claim 60 wherein the display is a video display.*

*62. A portable medical analyzer according to claim 53 including a communication port for sending results to an external or remote computer.*

*63. A portable medical analyzer according to claim 53 including:*

*(a) a removable analytical module mounted thereon;*

*(i) the removable analytical module mounted on the base unit being configured to make determinations characteristic of a fluid sample selected from blood or other body fluid removed from a patient.*

*64. A portable medical analyzer according to claim 53 including:*

*(a) an analytical module mounted on the base unit configured to make determinations characteristic of a fluid*

*sample selected from blood or other body fluid removed from a patient and selected from at least one of:*

(*i*) *pH;*

(*ii*) $pO_2$;

(*iii*) $pCO_2$;

(*iv*) $Na^+$;

(*v*) $Ca^{++}$;

(*vi*) $K^+$;

(*vii*) *hematocrit;*

(*viii*) *glucose;*

(*ix*) *general coagulation measurements; and*

(*x*) *co-oximetry measurements.*

*65. A portable medical analyzer according to claim 53 including:*

(*a*) *an analytical module permanently mounted on the base unit that includes a cartridge receptacle having a pair of guide flanges to hold, in use, a removable sample cartridge.*

*66. A portable medical analyzer according to claim 53 wherein:*

(*a*) *the base unit includes a temperature sensing device positioned to determine a temperature corresponding to a sample temperature in at least one removable sample cartridge, when the removable sample cartridge is mounted in an analytical module on the base unit.*

*67. A method comprising a step of:*

*operatively connecting a removable analytical module having a receiver for a disposable test unit to a portable medical analyzer comprising:*

(*a*) *a base unit having a main CPU and circuitry to process electrical signals generated by electrical, electrochemical, optical or mechanical sensors positioned in at least two analytical modules at least if and when each of the at least two analytical modules is operated to evaluate blood or other body fluid removed from a patient;*

(*b*) *one or more analytical module interface units for connecting and interfacing between one or more analytical modules and said base unit;*

(*c*) *the base unit being adapted to receive signals from at least two analytical modules, at least one of which is the removable analytical module, for making analytical determinations of blood or other body fluid removed from a patient; and, to connect, through a module interface unit, to the at least two analytical modules; and,*

(*d*) the base unit including programming logic and circuitry for receiving signals from the analytical modules when attached thereto, and directing an analytical output.

*68. A method according to claim 67 wherein:*

(*a*) *said step of operatively connecting a removable module comprises connecting the removable module to a portable medical analyzer already including a permanent analytical module adapted to receive a removable sample containing test device configured to evaluate at least one of pH,* $pO_2$, $pCO_2$, $Na^+$, $Ca^{++}$, $K^+$, *and hematocrit.*

* * * * *